(12) United States Patent
Ikeda et al.

(10) Patent No.: US 8,862,272 B2
(45) Date of Patent: Oct. 14, 2014

(54) REAGENT PREPARATION APPARATUS, REAGENT PREPARATION SYSTEM, AND REAGENT PREPARATION METHOD

(75) Inventors: Yutaka Ikeda, Kakogawa (JP); Noriyuki Nakanishi, Kakogawa (JP)

(73) Assignee: Sysmex Corporation, Hyogo (JP)

( * ) Notice: Subject to any disclaimer, the term of this patent is extended or adjusted under 35 U.S.C. 154(b) by 0 days.

(21) Appl. No.: 13/197,371

(22) Filed: Aug. 3, 2011

(65) Prior Publication Data

US 2012/0031175 A1    Feb. 9, 2012

(30) Foreign Application Priority Data

Aug. 4, 2010   (JP) ................................. 2010-175745

(51) Int. Cl.
 *G05B 21/00*    (2006.01)
 *G01N 1/38*    (2006.01)
 *G01N 35/10*    (2006.01)

(52) U.S. Cl.
 CPC .............. *G01N 1/38* (2013.01); *G01N 35/1002* (2013.01)
 USPC ........................ 700/266; 422/82.01

(58) Field of Classification Search
 CPC ........................... G01N 27/26; G01R 19/2513
 USPC ................ 700/271, 270, 266; 702/22, 23, 25; 422/617, 618, 82.01
 See application file for complete search history.

(56) References Cited

U.S. PATENT DOCUMENTS

| 6,290,856 B1 * | 9/2001 | Beall .............................. 210/753 |
| 2010/0055772 A1 | 3/2010 | Nagai et al. |
| 2010/0161243 A1 | 6/2010 | Nagai et al. |

FOREIGN PATENT DOCUMENTS

CN           101743477 A    6/2010

* cited by examiner

*Primary Examiner* — Natalia Levkovich
(74) *Attorney, Agent, or Firm* — Sughrue Mion, PLLC

(57) ABSTRACT

A reagent preparation apparatus for supplying a reagent, prepared by mixing a high concentration reagent and purified water supplied from a purified water production device, to a sample measurement device for measuring a sample using the prepared reagent, the reagent preparation apparatus comprising: a reagent preparation unit for preparing the reagent by mixing the high concentration reagent and the purified water supplied from the purified water production device; and a controller, communicably connected to the purified water production device, for controlling the purified water production device to continue producing the purified water until a predetermined time has elapsed from when the purified water production device starts the production of the purified water. Also, a reagent preparation system and a reagent preparation method.

19 Claims, 8 Drawing Sheets

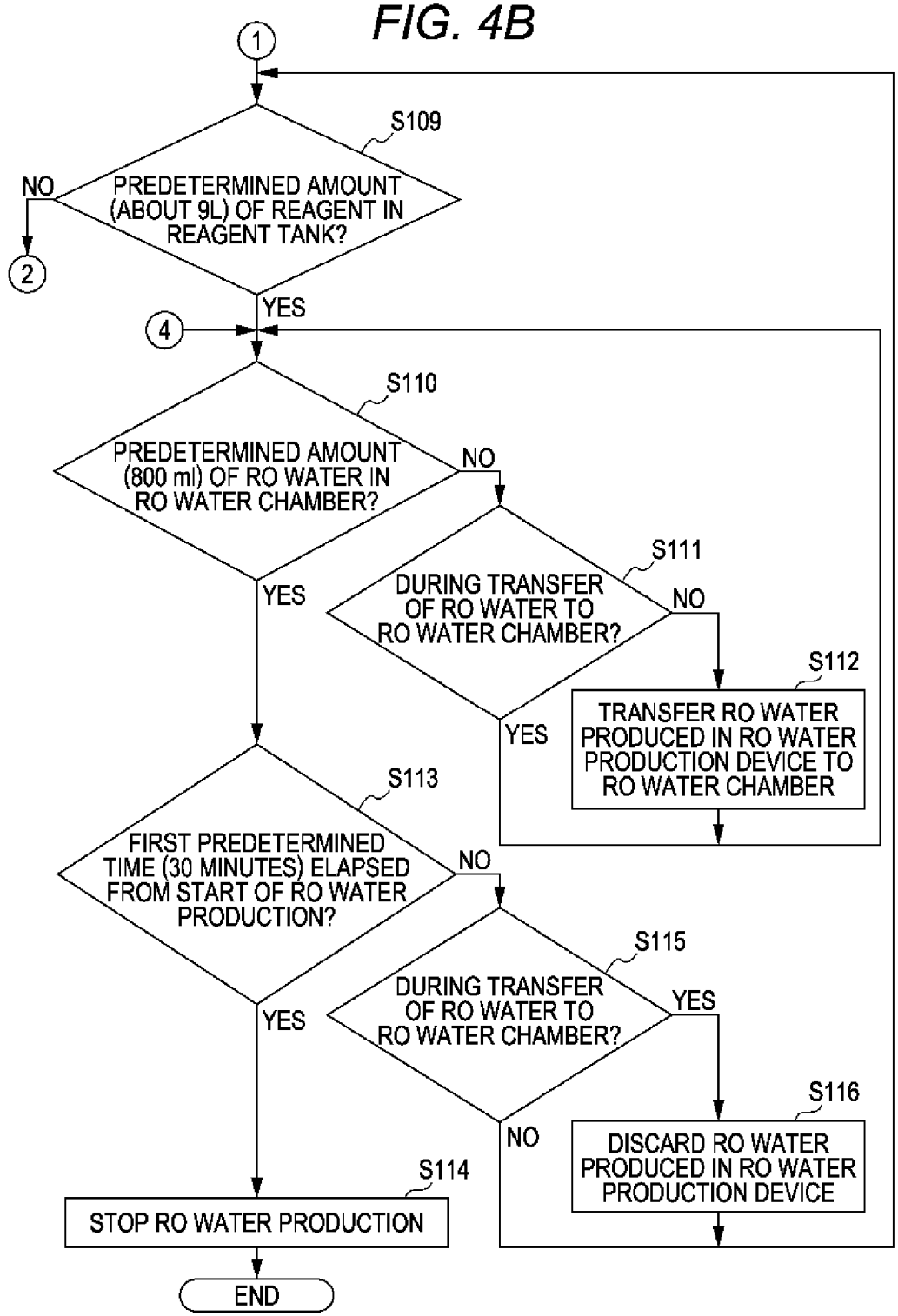

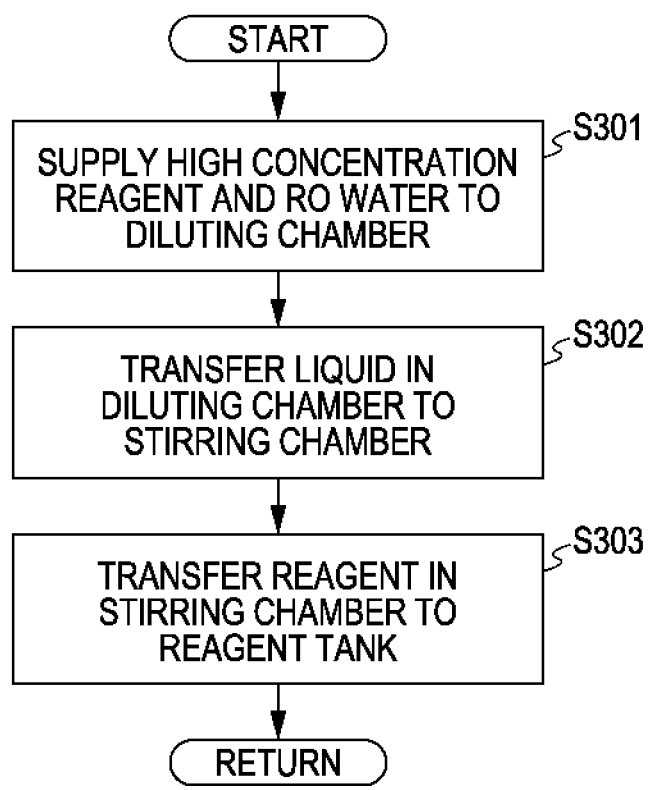

REAGENT PREPARATION APPARATUS, REAGENT PREPARATION SYSTEM, AND REAGENT PREPARATION METHOD

FIELD OF THE INVENTION

The present invention relates to a reagent preparation apparatus, a reagent preparation system, and a reagent preparation method for preparing a reagent used in a sample measurement by diluting a high concentration reagent using purified water.

BACKGROUND

A reagent preparation apparatus for preparing a reagent by mixing high concentration reagent and purified water is conventionally known. In a reagent preparation apparatus described in U.S. Patent Publication No. 2010/0055772, the purified water (RO water) produced in an RO (Reverse Osmosis) water producing section is stored in a RO water storage tank, and the RO water supplied from the RO water storage tank is used to prepare the reagent. In such reagent preparation apparatus, whether or not a predetermined amount of RO water is contained in the RO water storage tank is determined, and the RO water is produced by the RO water producing section if the predetermined amount of RO water is not stored in the RO water storage tank. The produced RO water is continuously supplied to the RO water storage tank if the RO water does not meet a predetermined amount, and the operation of the RO water production is stopped if the RO water of the RO water storage tank reached the predetermined amount.

In the reagent preparation apparatus described in U.S. Patent Publication No. 2010/0055772, the production of RO water is stopped when the RO water contained in the RO water storage tank reached the predetermined amount, and thereafter, the RO water is supplied from the RO water storage tank to prepare the reagent in a short time, and hence the RO water of the RO water storage tank again becomes lower than the predetermined amount and the production of the RO water is started. However, an operation for making ready to produce the RO water is necessary in the RO water producing section to resume the production of the RO water, and such operation requires time, and hence the production efficiency of the RO water lowers if production and stopping of the RO water are frequently repeated, and the reagent preparing process of the reagent preparing apparatus may not be efficiently carried out as a result. Furthermore, if production and stopping of the RO water are frequently repeated, the RO water production device connected to the reagent preparation apparatus may break down.

SUMMARY OF THE INVENTION

The scope of the present invention is defined solely by the appended claims, and is not affected to any degree by the statements within this summary.

According to a first aspect of the present invention, a reagent preparation apparatus for supplying a reagent, prepared by mixing a high concentration reagent and purified water supplied from a purified water production device, to a sample measurement device for measuring a sample using the prepared reagent, the reagent preparation apparatus comprising:

a reagent preparation unit for preparing the reagent by mixing the high concentration reagent and the purified water supplied from the purified water production device; and a controller, communicably connected to the purified water production device, for controlling the purified water production device to continue producing the purified water until a predetermined time has elapsed from when the purified water production device starts the production of the purified water.

According to a second aspect of the present invention, a reagent preparation system for supplying a reagent, prepared by mixing a high concentration reagent and purified water supplied from a purified water production device, to a sample measurement device for measuring a sample using the prepared reagent, the reagent preparation system comprising:

a purified water production device for producing the purified water; and a reagent preparation apparatus for mixing the high concentration reagent and the purified water supplied from the purified water production device to prepare the reagent, wherein the reagent preparation apparatus includes, a reagent preparation unit for preparing the reagent by mixing the high concentration reagent and the purified water supplied from the purified water production device; and a controller, communicably connected to the purified water production device, for controlling the purified water production device to continue producing the purified water until a predetermined time has elapsed from when the purified water production device starts the production of the purified water.

According to a third aspect of the present invention, a reagent preparation method of preparing a reagent by mixing a high concentration reagent and purified water from a purified water production device to supply the prepared reagent to a sample measurement device for measuring a sample using the prepared reagent, the reagent preparation method comprising steps of:

starting production of the purified water by the purified water production device;

continuing the production of the purified water by the purified water production device until a predetermined time has elapsed from start of production of the purified water by the purified water production device; and preparing the reagent by mixing the high concentration reagent and the purified water supplied from the purified water production device.

BRIEF DESCRIPTION OF THE DRAWINGS

FIG. 4B is a flowchart showing the operation procedure of the reagent preparation apparatus 4 according to the embodiment;

FIG. 6 is a flowchart showing the procedure of the second reagent supply process.

DETAILED DESCRIPTION OF THE PREFERRED EMBODIMENTS

Embodiments of the present invention will be hereinafter described based on the drawings.

[Configuration of Sample Analyzing System]

Figure 1:
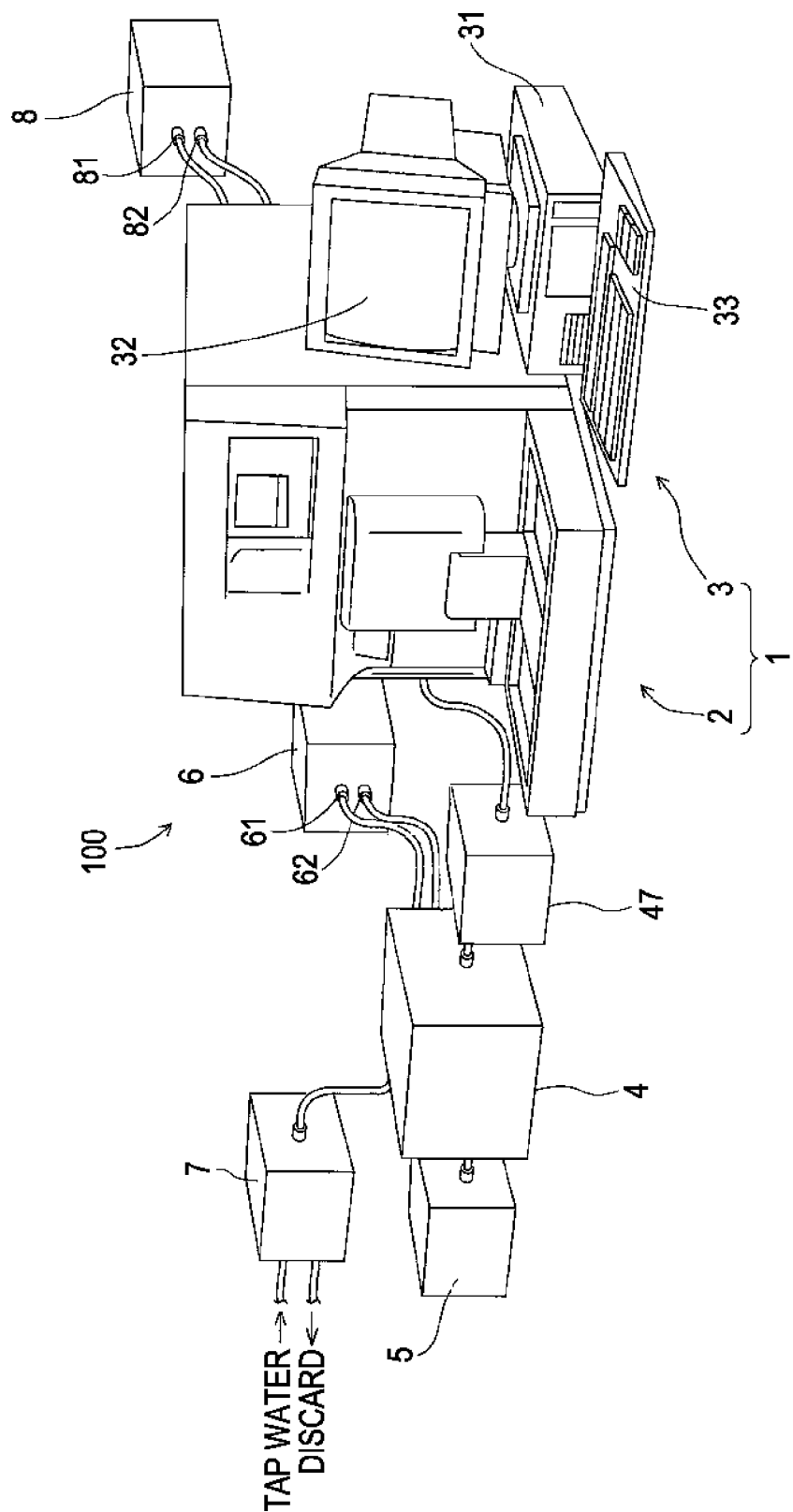
FIG. 1 is a perspective view showing a configuration of a sample analyzing system according to an embodiment.

FIG. 1 is a perspective view showing a configuration of a sample analyzing system according to the present embodiment. A sample analyzing system 100 according to the present embodiment includes a blood analyzer 1, a reagent preparation apparatus 4, and a RO water production device 7. The reagent preparation apparatus 4 is connected to the blood analyzer 1 and the RO water production device 7, where the reagent is prepared using purified water (RO water) supplied from the RO water production device 7, and the prepared reagent is supplied to the blood analyzer 1.

As shown in FIG. 1, the blood analyzer 1 includes a measurement section 2 having a function of carrying out measurement of blood, and a data processing section 3 for analyzing measurement data output from the measurement section 2 and obtaining an analysis result. The measurement section 2 is configured to measure the white blood cells, the reticulocytes, and the blood platelets in the blood through the flow cytometry method. The measurement section 2 is configured to dilute blood using the reagent prepared and supplied by the reagent preparation apparatus 4, and measure the white blood cells, the reticulocytes, and the blood platelets. The flow cytometry method is a measurement method of forming a sample flow including the measurement specimen and irradiating a laser light onto the sample flow to measure the particles (blood cells) for detecting forward scattered light, lateral scattered light, and lateral fluorescence emitted by the particles (blood cells) in the measurement specimen.

The measurement section 2 is connected with a pneumatic section 8 installed exterior to the housing, where transfer of various types of liquid is carried out in the apparatus using the negative pressure and the positive pressure supplied from the pneumatic section 8. The pneumatic section 8 includes a negative pressure source 81 for supplying negative pressure to the measurement section 2, and a positive pressure source 82 for supplying positive pressure. The reagent to be used in the measurement is aspirated from the reagent preparation apparatus 4 to the measurement section 2 (reagent is supplied from the reagent preparation apparatus 4) by using the negative pressure of the negative pressure source 81.

The data processing section 3 is configured by a personal computer (PC), and has a function of analyzing the measurement data of the measurement section 2 and displaying the analysis result. The data processing section 3 includes a control unit (PC main body) 31, a display unit 32 and an input device 33.

The control unit 31 is communicably connected to the measurement section 2 and the reagent preparation apparatus 4 through a communication interface (not shown), and has a function of transmitting a measurement start signal and a shutdown signal to the measurement section 2 and the reagent preparation apparatus 4 in addition to receiving the measurement data of the measurement section 2. The user uses the input device 33 to carryout selection of measurement mode, startup and shut down of the measurement section 2, and the like.

The display unit 32 displays an image (screen) according to a video signal input, by the control unit 31. The data processing section 3 is configured to collect operation information of the measurement section 2 by the control unit 31 and display the same on the display unit 32 so that notification of abnormality and notification of various types of information such as elapse of analyzing process can be made to the user.

<Configuration of Reagent-Preparation Apparatus>

Figure 2:
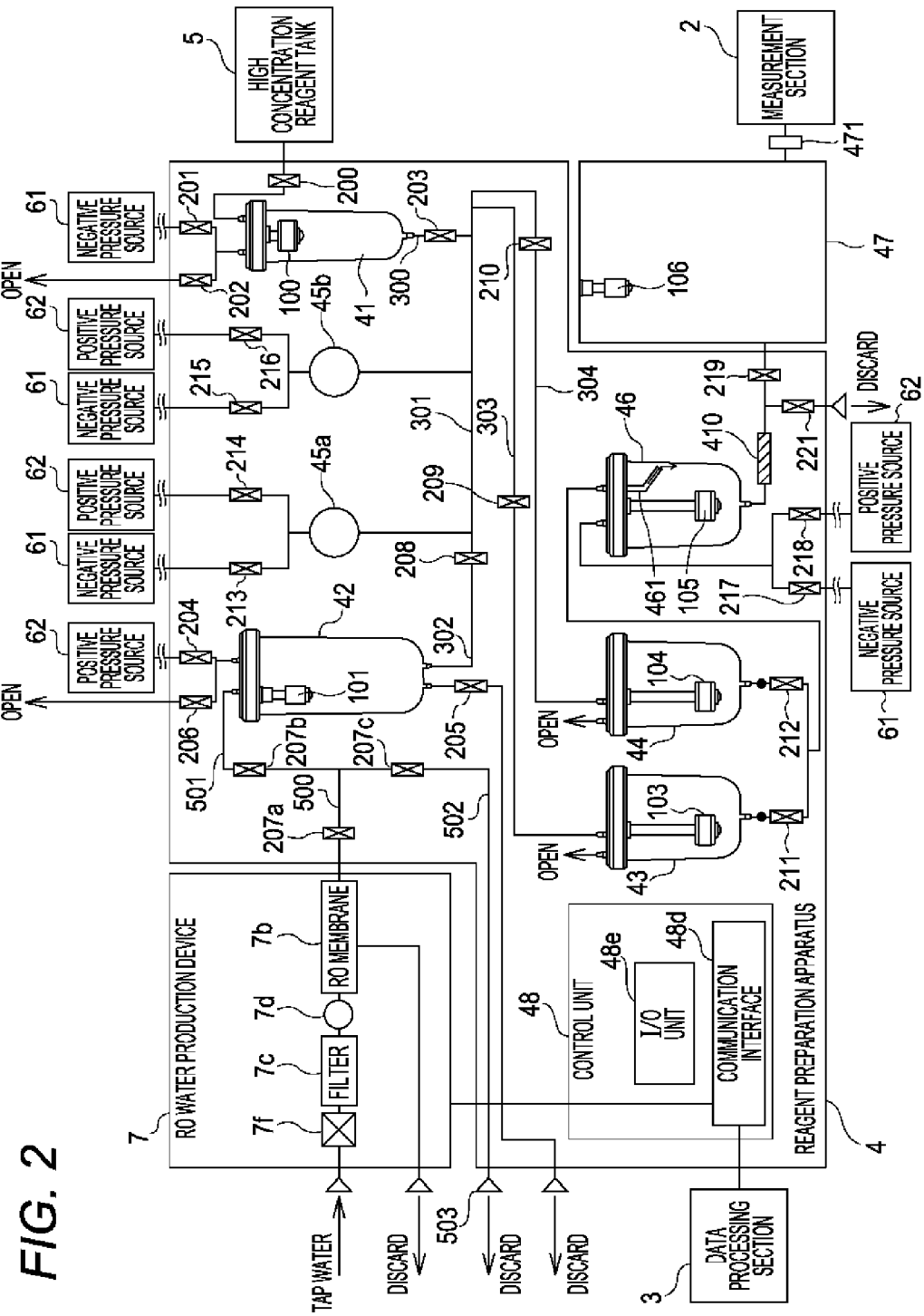
FIG. 2 is a fluid circuit diagram showing a configuration of a reagent preparation apparatus 4 according to the embodiment.

FIG. 2 is a fluid circuit diagram showing a configuration of the reagent preparation apparatus 4 according to the present embodiment. The reagent preparation apparatus 4 according to the present embodiment is arranged to prepare the reagent used in the measurement section 2. Specifically, the reagent preparation apparatus 4 is configured to prepare the reagent used for blood analysis by diluting the high concentration reagent (reagent undiluted solution) to a desired concentration using the RO water produced from tap water. The RO water is one type of purified water, and is water in which impurities are removed by being transmitted through the RO (Reverse Osmosis) film (reverse osmosis membrane). The purified water includes purified water, deionized water, and distilled water, and is water subjected to the process of removing the impurities.

As shown in FIG. 2, the reagent preparation apparatus 4 includes a high concentration reagent chamber 41, an RO water chamber 42, a first diluting chamber 43 and a second diluting chamber 44, two diaphragm pumps 45a and 45b, a stirring chamber 46, a reagent tank 47, and a control unit 48 for controlling the operation of each unit of the reagent preparation apparatus 4. Furthermore, as shown in FIG. 1, the reagent preparation apparatus 4 is connected to the high concentration reagent tank installed exterior to the housing, the pneumatic section 6, and the RO water production device 7. The reagent preparation apparatus 4 acquires the high concentration reagent and the RO water from the high concentration reagent tank 5 and the RO water production device 7, respectively, and transfers each liquid in the apparatus using the negative pressure and the positive pressure supplied from the pneumatic section 6. The pneumatic section 6 includes a negative pressure source 61 for supplying negative pressure to the reagent preparation apparatus 4, and a positive pressure source 62 for supplying positive pressure.

As shown in FIG. 2, the high concentration reagent chamber 41 is configured such that the high concentration reagent is supplied from the high concentration reagent tank 5. The high concentration reagent chamber 41 includes a float switch 100 for detecting that a predetermined amount of high concentration reagent is contained in the chamber. The float switch 100 is configured such that a float portion moves up and down according to the liquid amount (liquid level) in the high concentration reagent chamber 41, where each unit is controlled by the control unit 48 so that when the float portion of the float switch 100 reaches the lower limit, the high concentration reagent is supplied from the high concentration reagent tank 5 to the high concentration reagent chamber 41 until the float portion reaches the upper limit. The high concentration reagent is supplied to the high concentration reagent chamber 41 so that about 300 mL is always stored.

The high concentration reagent chamber 41 is connected to the high concentration reagent tank 5 through an electromagnetic valve 200, and is connected to the negative pressure source 61 of the pneumatic section 6 through an electromagnetic valve 201. The high concentration reagent chamber 41 is configured to open to atmosphere and close by the opening and closing of an electromagnetic valve 202. The high concentration reagent chamber 41 is connected to a flow path 301 for transferring liquid from a diaphragm pump 45a (45b) to the first diluting chamber 43 (second diluting chamber 44) by a flow path 300. An electromagnetic valve 203 is arranged on the flow path 300, and the flow-in of the high concentration reagent to the flow path 301 is controlled by the opening and closing of the electromagnetic valve 203.

The RO water chamber 42 is configured so that the RO water for diluting the high concentration reagent is supplied from the RO water production device 7. The RO water chamber 42 includes a float switch 101 for detecting that the RO water contained in the chamber reached a predetermined amount (about 800 mL). The float switch 101 is configured such that the float portion moves up and down according to the liquid amount (liquid level) in the RO water chamber 42. When the float portion of the float switch 101 reaches a position corresponding to the predetermined amount (about 800 mL) of the RO water chamber 42 or higher, each unit is controlled by the control unit 48 so that the supply of RO water from the RO water production device 7 to the RO water chamber 42 is stopped. When the float portion of the float switch 101 is positioned below the position corresponding to the predetermined amount (about 800 mL) of the RO water chamber 42, each unit is controlled by the control unit 48 so that the supply of RO water from the RO water production device 7 to the RO water chamber 42 is started.

The RO water chamber 42 is configured to be able to discard the RO water in the chamber. Specifically, the RO water chamber 42 is connected to the positive pressure source 62 through an electromagnetic valve 204, and is connected to a discarding flow path through an electromagnetic valve 205, so that the RO water inside is pushed out to the discarding flow path by the positive pressure by opening both electromagnetic valves 204 and 205. The RO water chamber 42 is configured to open to atmosphere and close by the opening and closing of an electromagnetic valve 206. The RO water chamber 42 is connected to the diaphragm pumps 45a and 45b by the flow path 302 through the electromagnetic valve 208.

In the present embodiment, the RO water production device 7 and the reagent preparation apparatus 4 are connected through a flow-in control valve 207a, and the flow-in (supply) of the RO water to the flow path 500 in the reagent preparation apparatus 4 is controlled by the opening and closing of the flow-in control valve 207a. The flow path 500 is a branched path, and the flow path 500 is connected to a flow path 501 for supplying the RO water to the RO water chamber 42, and a flow path 502 connected to a discarding port 503 for discarding the RO water that flowed in. The flow path 500 and the flow path 501 are connected through a supply valve 207b, and the flow path 500 and the flow path 502 are connected through a discarding valve 207c. Therefore, when the flow-in control valve 207a and the supply valve 207b are opened with the discarding valve 207c closed, the RO water supplied from the RO water production device 7 flows into the RO water chamber 42 through the flow path 500 and the flow path 501. Furthermore, when the flow-in control valve 207a and the discarding valve 207c are opened with the supply valve 207b closed, the RO water supplied from the RO water production device 7 is discarded from the discarding port 503 through the flow path 500 and the flow path 502. Therefore, the supply valve 207b and the discarding valve 207c are respectively configured to function as a flow path switching portion of the flow paths 501 and 502.

As shown in FIG. 2, the first diluting chamber 43 and the second diluting chamber 44 are respectively arranged to dilute the high concentration reagent with the RO water. The first diluting chamber 43 (second diluting chamber 44) is configured to accommodate about 300 mL of liquid (mixed solution of high concentration reagent and RO water) sent by the diaphragm pumps 45a and 45b, as hereinafter described. The first diluting chamber 43 (second diluting chamber 44) includes a float switch 103 (104) that can move up and down for detecting that the remaining amount of the liquid (mixed solution of high concentration reagent and RO water) contained in the chamber is substantially zero. The first diluting chamber 43 (second diluting chamber 44) is configured to always be in a state opened to atmosphere. The first diluting chamber 43 (second diluting chamber 44) is connected to the flow path 301 by the flow path 303 (304) through an electromagnetic valve 209 (210). Whether to supply the liquid (RO water and high concentration reagent) transferred through the flow path 301 from the flow path 303 to the first diluting chamber 43 or to supply from the flow path 304 to the second diluting chamber 44 can be selected by controlling the opening and closing of the electromagnetic valves 209 and 210. The first diluting chamber 43 (second diluting chamber 44) is connected to a stirring chamber 46 through an electromagnetic valve 211 (212).

The diaphragm pumps 45a and 45b have similar configurations with respect to each other, and are configured to carryout the same operation at the same time. The diaphragm pump 45a (45b) has a function of quantifying the high concentration reagent and the RO water respectively by about 6.0 mL (constant amount) in one quantitative operation, and is configured to supply a total of about 12 mL (about 6.0 mL×2) of liquid in one quantification. The diaphragm pump 45a (45b) is connected to the negative pressure source 61 through an electromagnetic valve 213 (215), and is connected to the positive pressure source 62 through an electromagnetic valve 214 (216).

The supplying operation of the liquid (RO water and high concentration reagent) by the diaphragm pumps 45a and 45b includes two processes of the flow-in of the liquid by the negative pressure source 61 through the electromagnetic valve 213 (215), and the flow-out of the liquid by the positive pressure source 62 through the electromagnetic valve 214 (216). In the respective process, a predetermined flow path is selected from the flow paths 300 to 304 with the opening and closing control of the electromagnetic valves 203, 208, 209, and 210, so that the high concentration reagent or the RO water flows in from the high concentration reagent chamber 41 or the RO water chamber 42, and quantifying is carried out for every about 12 mL (about 6.0 mL×2) to the first diluting chamber 43 or the second diluting chamber 44 so that the liquid is supplied over plural times.

The stirring chamber 46 is configured to be able to accommodate about 300 mL of liquid, and is arranged to stir the liquid (mixed solution of high concentration reagent and RO water) supplied from the first diluting chamber 43 (second diluting chamber 44). Specifically, the stirring chamber 46 is configured to include a bent pipe 461, so that the liquid (mixed solution of high concentration reagent and RO water) supplied from the first diluting chamber 43 (second diluting chamber 44) flow along the inner wall surface of the stirring chamber 46 thus generating a convection and stirring the high concentration reagent and the RO water.

The stirring chamber 46 includes a float switch 105 that can move up and down for detecting that the remaining amount of the liquid (mixed solution of high concentration reagent and RO water) contained in the chamber is substantially zero. When transferring the liquid from the first diluting chamber 43 to the stirring chamber 46, the control unit 48 opens the electromagnetic valve 211 and the electromagnetic valve 217, and closes the electromagnetic valve 212 and the electromagnetic valve 218. About 300 mL of liquid (mixed solution of high concentration reagent and RO water) is thereby supplied from the first diluting chamber 43 to the stirring chamber 46. When transferring the liquid from the second diluting chamber 44 to the stirring chamber 46, the control unit 48 opens the electromagnetic valve 212 and the electromagnetic valve 217, and closes the electromagnetic valve 211 and the electromagnetic valve 218. About 300 mL of liquid (mixed solution of high concentration reagent and RO water) is thereby supplied from the second diluting chamber 44 to the stirring chamber 46.

The mixed solution of the high concentration reagent and the RO water is stirred by the stirring chamber 46, and the reagent of desired concentration is prepared. The reagent of desired concentration is supplied from the stirring chamber 46 to the reagent tank 47 arranged exterior to the reagent preparation apparatus 4. The reagent tank 47 is arranged to accommodate and store the reagent waiting to be supplied to the measurement section 2. The reagent tank 47 can accommodate the reagent (stirred mixed solution having predetermined concentration) of a maximum liquid amount of about 9 L. The reagent tank 47 includes a float switch 106 for detecting that the remaining amount of the reagent accommodated in the chamber reached about 9 L, and a float switch 107 for detecting that the remaining amount of the reagent is substantially zero. The float switch 106 (107) is configured such that the float portion moves up and down according to the liquid amount (liquid level) in the reagent tank 47. About 300 mL (total amount of reagent prepared by one preparing operation in the stirring chamber 46) of reagent of the desired concentration is supplied from the stirring chamber 46 to the reagent tank 47 in one time according to the control of each portion of the control unit 48.

When detection is made that the remaining amount of reagent accommodated in the reagent tank 47 is substantially zero by the float switch 107, the supply of reagent to the measurement section 2 is stopped. Therefore, air bubbles can be prevented from mixing in the reagent to supply to the measurement section 2 while continuing the supply of reagent to the measurement section 2 as much as possible even if the reagent is not supplied to the reagent tank 47 for some reason.

The reagent tank 47 is connected to the stirring chamber 46 through an electromagnetic valve 219. The reagent tank 47 is configured to always be in a state opened to atmosphere. The reagent tank 47 is connected to the measurement section 2 through a filter 471. The filter 471 is arranged to prevent impurities from mixing in the reagent to be supplied to the measurement section 2.

In the present embodiment, the reagent preparation apparatus 4 includes an electrical conductivity measurement unit 410. The electrical conductivity measurement unit 410 is arranged between the stirring chamber 46 and the reagent tank 47. The electrical conductivity measurement unit 410 includes an electrical conductivity meter and a temperature sensor (thermistor), and has a function of measuring the electrical conductivity of the reagent at a position where the electrical conductivity measurement unit 410 is arranged. Since the concentration of the reagent and the electrical conductivity have a predetermined relationship, the concentration of the prepared reagent can be determined by measuring the electrical conductivity of the reagent (mixed solution) in which the RO water and the high concentration reagent are mixed. A discarding flow path is connected through an electromagnetic valve 221 between the electrical conductivity measurement unit 410 and the electromagnetic valve 219. If the measured concentration of the reagent is not the desired concentration, such reagent is discarded from the discarding flow path.

As shown in FIG. 2, the RO water production device 7 connected to the reagent preparation apparatus 4 is configured to be able to produce the RO water serving as a diluting liquid for diluting the high concentration reagent using tap water. The RO water production device 7 includes an RO water storage tank 7a, an RO membrane 7b, and a filter 7c for protecting the RO membrane 7b by removing impurities in the tap water. The RO water production device 7 also includes a high pressure pump 7d for applying high pressure on the water that passed through the filter 7c so that water molecules transmit through the RO membrane 7b, and an electromagnetic valve 7f for controlling the supply of tap water.

In the present embodiment, the speed at which the RO water is supplied from the RO water production device 7, that is, the production speed of the RO water by the RO water production device 7 is about 5 L/hour, and the time required for the preparing operation to start the RO water production is about 5 minutes.

Figure 3:
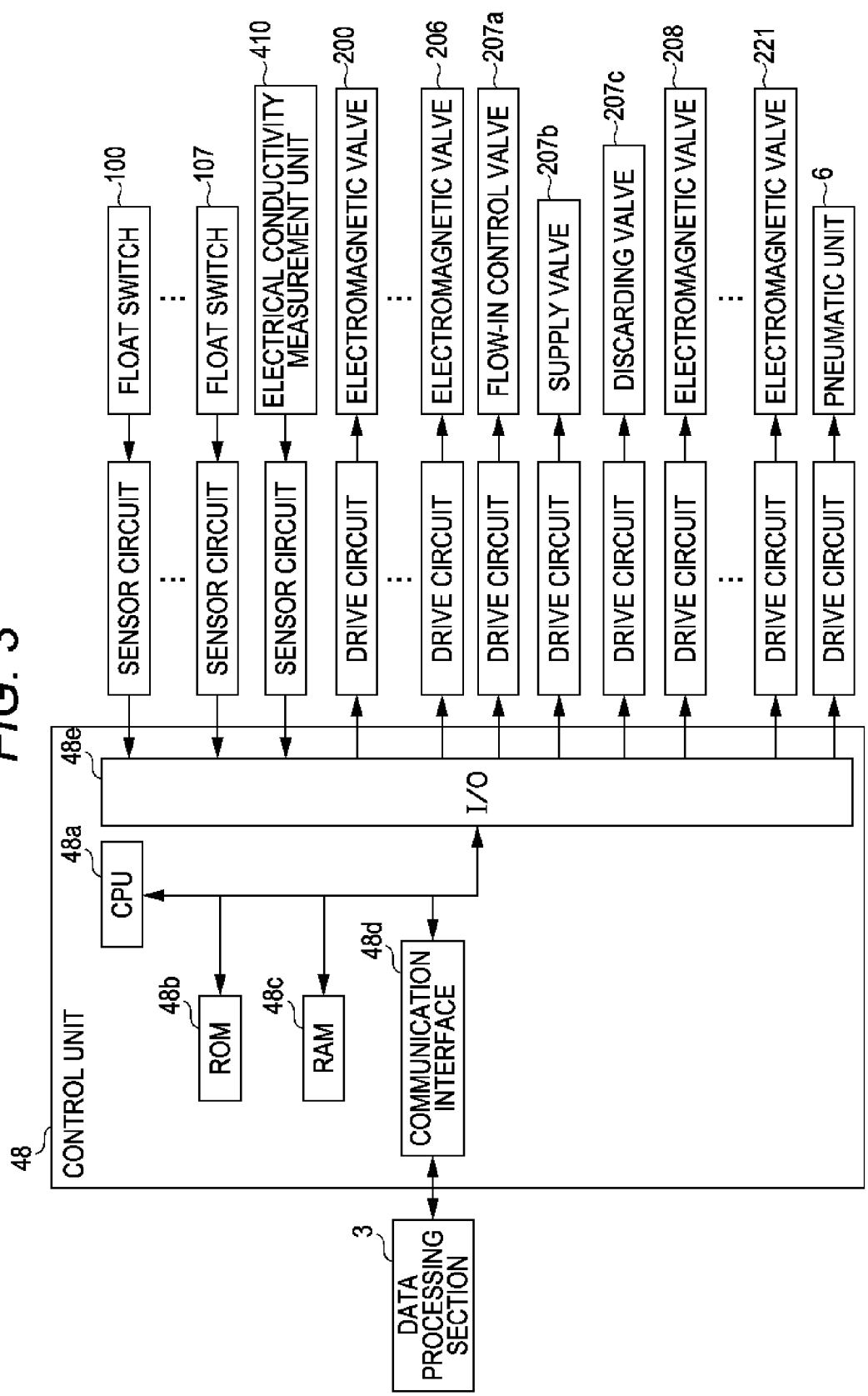
FIG. 3 is a block diagram showing the configuration of a control unit of the reagent preparation apparatus 4 according to the embodiment.

FIG. 3 is a block diagram showing a configuration of the control unit of the reagent preparation apparatus 4 according to the present embodiment. As shown in FIG. 3, the control unit 48 includes a CPU 48a, a ROM 48b, a RAM 48c, a communication interface 48d connected to the data processing section 3, and an I/O (Input/Output) unit 48e connected to each section of the reagent preparation apparatus 4 through each circuit.

The CPU 48a is arranged to execute the computer program stored in the ROM 48b and the computer program loaded in the RAM 48c. In executing the computer programs, the CPU 48a uses the RAM 48c as a work region. The function of the computer program stored in the ROM 48b and the computer program loaded in the RAM 48c includes a timing function of carrying out time measurement from the transmission of a command to start the production of the RO water to the RO water production device 7, and the time measurement on how long a state in which the amount of RO water contained in the RO water chamber 42 reached a predetermined amount (about 800 mL) is continued.

The communication interface 48d is data communicably connected to each of the data processing section 3 and the RO water production device 7. The control unit 48 thus can transmit a command instructing the start of production of the RO water and the stop of production of the RO water with respect to the RO water production device 7 to the RO water production device 7. The error information, operation state information, and the like of the reagent preparation apparatus 4 are transmitted from the communication interface 48d to the data processing section 3, and the error notification, operation state notification, or the like are displayed by the data processing section 3.

As shown in FIG. 3, the I/O unit 48e is configured to receive signals from the float switches 100 to 107, and the electrical conductivity measurement unit 410 through each sensor circuit. The I/O unit 48e is configured to output a signal to each drive circuit to control the drive of the electromagnetic valves 200 to 206, the flow-in control valve 207a, the supply valve 207b, the discarding valve 207c, the electromagnetic valves 208 to 221, and the pneumatic section 6 through each drive circuit.

[Operation of Reagent Preparation Apparatus]

The operation of the reagent preparation apparatus 4 according to the present embodiment will now be described.

Figure 4A:
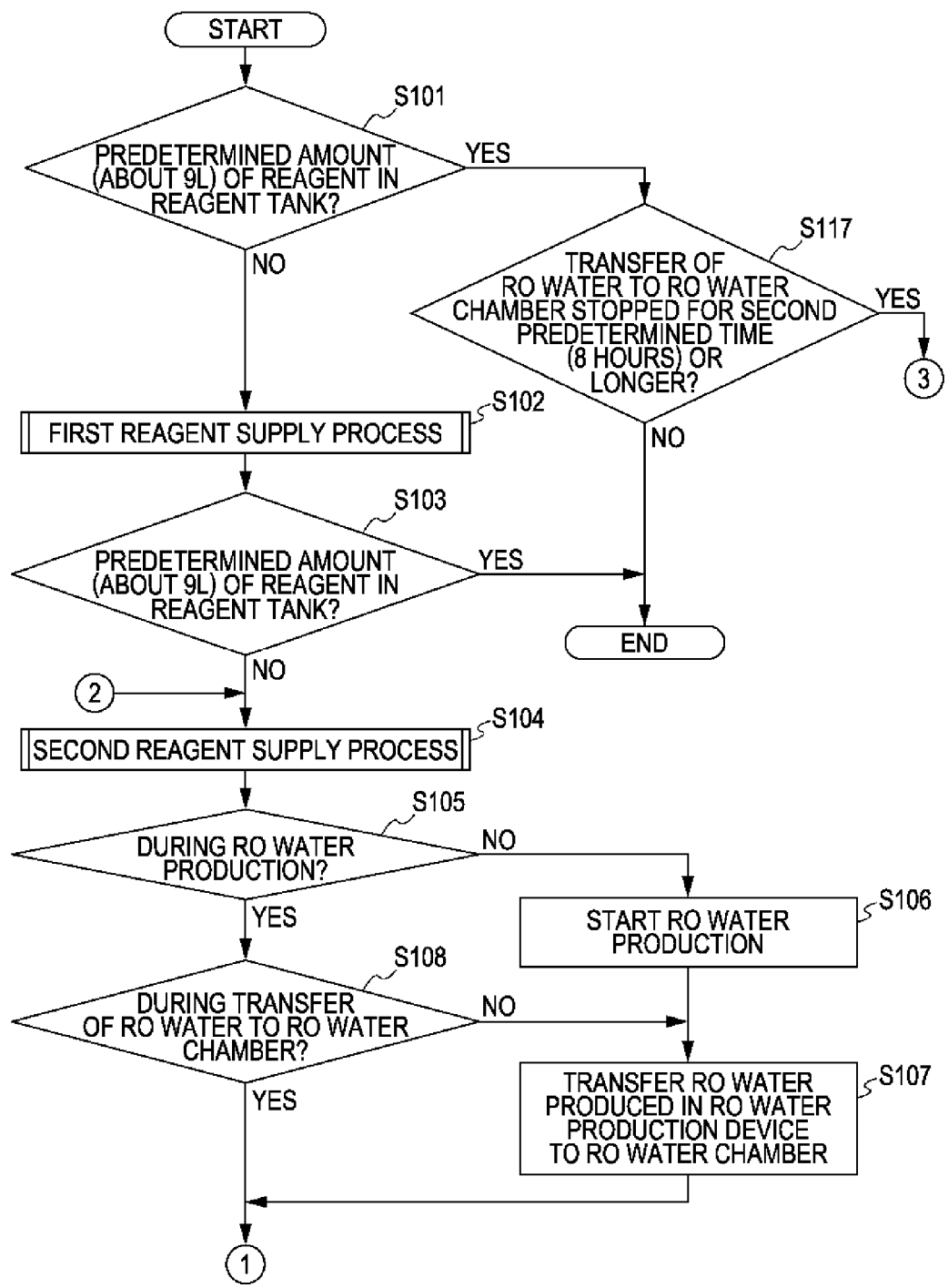
FIG. 4A is a flowchart showing the operation procedure of the reagent preparation apparatus 4 according to the embodiment.
Figure 4C:
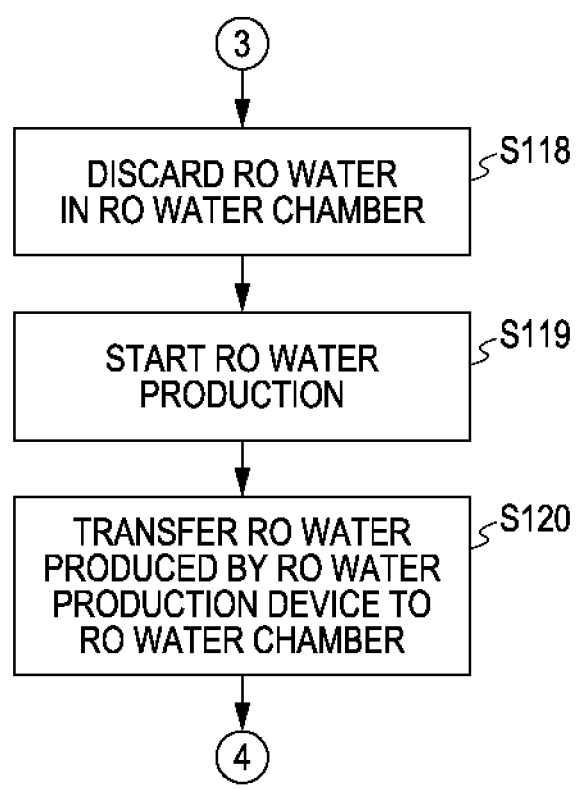
FIG. 4C is a flowchart showing the operation procedure of the reagent preparation apparatus 4 according to the embodiment.

FIG. 4A to FIG. 4C are flowcharts showing the operation procedure of the reagent preparation apparatus 4 according to the present embodiment. In the reagent preparation apparatus 4 according to the present embodiment, the RO water is produced by the RO water production device 7 after the apparatus is started and supplied to the RO water chamber 42, so that a predetermined amount (about 800 mL) of RO water is stored in the RO water chamber 42. The production of the RO water of the RO water production device 7 is stopped in this state, and the RO water production device 7 transitions to the standby state (state in which RO water production can be started). When a predetermined amount of RO water is stored in the RO water chamber 42 and the RO water production device 7 is in the standby state, the reagent preparation apparatus 4 starts the reagent preparing operation described below. The start of the RO water production is triggered by the transmission of the command to start the production of the RO water to the RO water production device 7, and the stopping of the RO water production is triggered by the transmission of the command to stop the production of the RO water to the RO water production device 7.

First, the CPU 48a determines whether or not a predetermined amount (about 9 L) of reagent is accommodated in the reagent tank 47 based on the output signal of the float switch 106 (step S101). If a predetermined amount (about 9 L) of reagent is not accommodated in the reagent tank 47 (NO in step S101), the CPU 48a executes a first reagent supply process (step S102).

Figure 5:
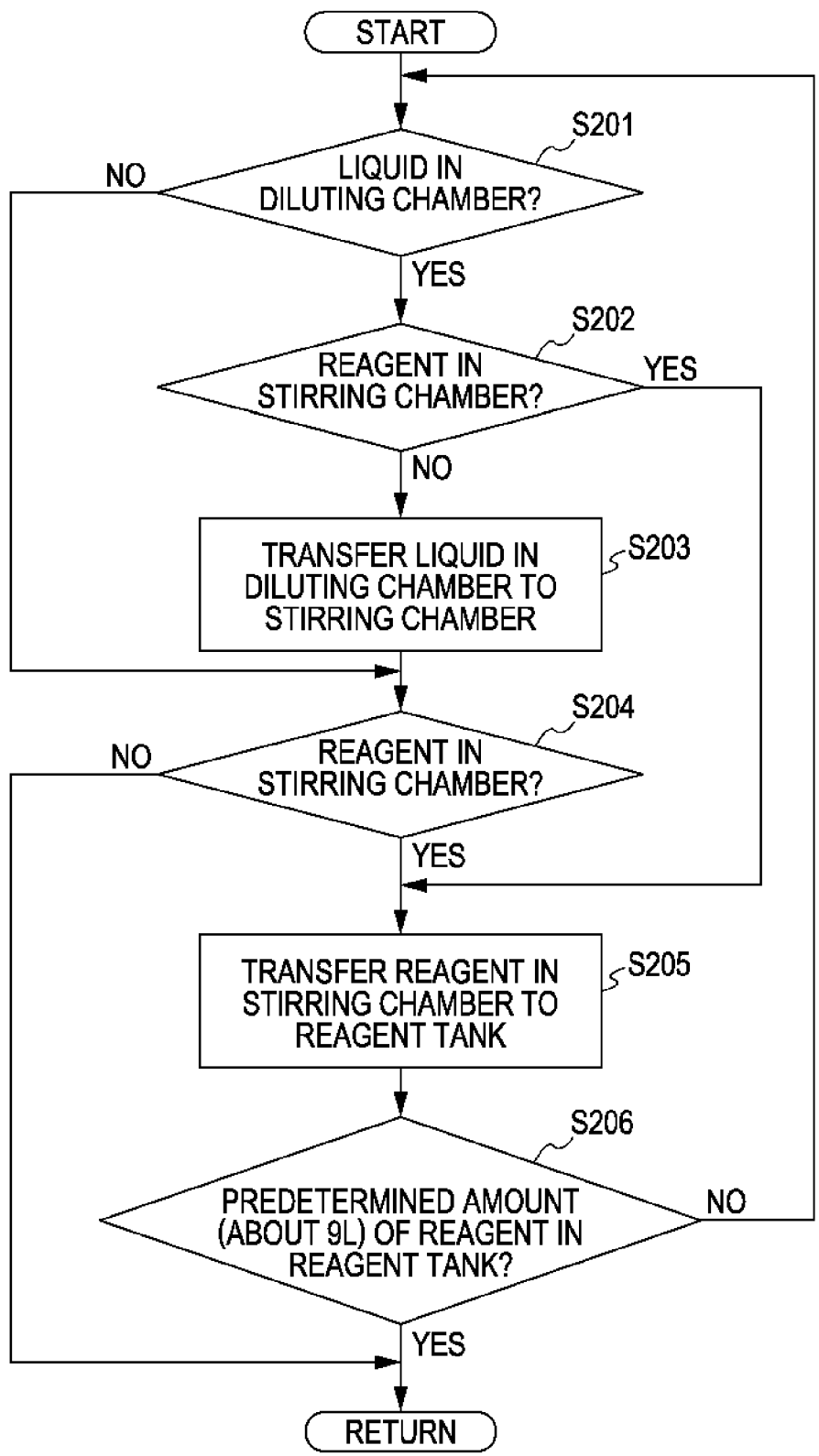
FIG. 5 is a flowchart showing the procedure of the first reagent supply process.

FIG. 5 is a flowchart showing the procedure of the first reagent supply process. In the first reagent supply process, the CPU 48a first determines whether or not liquid (mixed solution of high concentration reagent and RO water) is accommodated in the first diluting chamber 43 or the second diluting chamber 44, that is, whether or not the remaining amount of liquid accommodated in the first diluting chamber 43 or the second diluting chamber 44 is substantially zero based on the output signals of the float switches 103 and 104 (step S201). If the liquid is not accommodated in both the first diluting chamber 43 and the second diluting chamber 44 in step S201 (NO in step S201), the CPU 48a proceeds the process to step S204. If the liquid is accommodated in at least one of either the first diluting chamber 43 or the second diluting chamber 44 in step S201 (YES in step S201), the CPU 48a determines whether or not the liquid is accommodated in the stirring chamber 46 based on the output signal of the float switch 105 (step S202).

If the liquid is accommodated in the stirring chamber 46 in step S202 (YES in step S202), the CPU 48a proceeds the process to step S205. If the liquid is not accommodated in the stirring chamber 46 in step S202 (NO in step S202), the CPU 48a controls the electromagnetic valves 211, 212, 217, 218 to transfer the liquid from one of either the first diluting chamber 43 or the second diluting chamber 44 that accommodates the liquid to the stirring chamber 46 (step S203), and proceeds the process to step S204.

In step S204, the CPU 48a determines whether or not liquid is accommodated in the stirring chamber 46 based on the output signal of the float switch 105 (step S204). If the liquid is not accommodated in the stirring chamber 46 in step S204 (NO in step S204), the CPU 48a returns the process to the callout address of the first reagent supply process in the main routine. If the liquid is accommodated in the stirring chamber 46 in step S204 (YES in step S204), the CPU 48a proceeds the process to step S205.

In step S205, the CPU 48a opens the electromagnetic valve 219 and transfers the reagent from the stirring chamber 46 to the reagent tank 47 (step S205).

The CPU 48a then determines whether or not a predetermined amount (about 9 L) of reagent is accommodated in the reagent tank 47 based on the output signal of the float switch 106 (step S206). If a predetermined amount (about 9 L) of reagent is not accommodated in the reagent tank 47 (NO in step S206), the CPU 48a returns the process to step S201. If a predetermined amount (about 9 L) of reagent is accommodated in the reagent tank 47 in step S206 (YES in step S206), the CPU 48a returns the process to the callout address of the first reagent supply process in the main routine.

The reagent prepared from the liquid accommodated in the first diluting chamber 43 and the second diluting chamber 44 as well as the reagent accommodated in the stirring chamber 46 are transferred to the reagent tank 47 until the amount of reagent of the reagent tank 47 reaches a predetermined amount (about 9 L) with the RO water production by the RO water production device 7 stopped by the first reagent supply process.

After the first reagent supply process is terminated, the CPU 48a determines whether or not a predetermined amount (about 9 L) of reagent is accommodated in the reagent tank 47 based on the output signal of the float switch 106 (step S103). That is, whether or not the amount of reagent in the reagent tank 47 reached a predetermined amount is determined as a result of supplying the reagent to the reagent tank 47 in the first reagent supply process.

If a predetermined amount (about 9 L) of reagent is accommodated in the reagent tank 47 in step S103, that is, if the amount of reagent in the reagent tank 47 reached about 9 L (i.e., maximum amount of reagent that can be accommodated in the reagent tank 47) by the first reagent supply process (YES in step S103), the CPU 48a terminates the process.

If a predetermined amount (about 9 L) of reagent is not accommodated in the reagent tank 47 in step S103, that is, if the amount of reagent in the reagent tank 47 does not reach about 9 L by the first reagent supply process (NO in step S103), the CPU 48a executes a second reagent supply process (step S104).

FIG. 6 is a flowchart showing the procedure of the second reagent supply process. A predetermined amount (about 800 mL) of RO water is accommodated in the RO water chamber 42 at the time point the second reagent supply process is executed. First, the CPU 48a supplies the high concentration reagent and the RO water to either the first diluting chamber 43 or the second diluting chamber 44 in which the liquid is not accommodated by the diaphragm pumps 45a and 45b (step S301). In this case, 12 mL of RO water is supplied 24 times, and 12 mL of high concentration reagent is supplied once to the first diluting chamber 43 or the second diluting chamber 44. That is, the high concentration reagent is diluted to 25 times by the RO water.

The CPU 48a then controls the electromagnetic valves 211, 212, 217, 218 to transfer the liquid from one of the first diluting chamber 43 and the second diluting chamber 44 in which the liquid is accommodated to the stirring chamber 46 (step S302). The mixed solution of the high concentration reagent and the RO water accommodated in the first diluting chamber 43 or the second diluting chamber 44 is thereby stirred, and the reagent in which the high concentration reagent is diluted to 25 times is prepared.

The CPU 48a then opens the electromagnetic valve 219, transfers the reagent from the stirring chamber 46 to the reagent tank 47 (step S303), and returns the process to the callout address of the second reagent supply process in the main routine.

According to the second reagent supply process, the reagent is prepared using the RO water accommodated in the RO water chamber 42 and the high concentration reagent accommodated in the high concentration reagent tank 5 with the RO water production by the RO water production device 7 stopped, and the prepared reagent is transferred to the reagent tank 47. The amount of reagent supplied to the reagent tank 47 by the execution of the second reagent supply process of one time is about 300 mL.

When the second reagent supply process is executed, the RO water accommodated in the RO water chamber 42 is consumed in the reagent preparation, and the water level of the RO water chamber 42 becomes lower than a predetermined water level (800 mL). The CPU 48a thus determines whether or not the production of the RO water by the RO water production device 7 has started (step S105), where if the RO water production has not started (NO in step S105), the CPU 48a transmits a command to the RO water production device 7 to control the RO water production device 7 and start the production of the RO water (step S106), and controls the flow-in control valve 207a, the supply valve 207b, and the discarding valve 207c to transfer the RO water produced by the RO water production device 7 to the RO water chamber 42 (step S107). The RO water is thereby supplied from the RO water production device 7 to the reagent preparation apparatus 4, and the RO water is stored in the RO water chamber 42. The processes of steps S105 to S107 are executed in parallel to the second reagent supply process. That is, the production of the RO water and the supply of the RO water to the reagent preparation apparatus 4 are carried out while executing the second reagent supply process.

The CPU 48a proceeds the process to step S109 after starting the production of the RO water. If the production of the RO water is already started in step S105 (YES in step S105), the CPU 48a determines whether or not the RO water produced by the RO water production device 7 is transferred to the RO water chamber 42 (step S108). That is, whether or not the RO water produced by the RO water production device 7 is discarded is determined, as will be hereinafter described. If the RO water produced by the RO water production device is not transferred to the RO water chamber 42, that is, if the RO water produced by the RO water production device 7 is discarded in step S108 (NO in step S108), the CPU 48a proceeds the process to step S107, controls the flow-in control valve 207a, the supply valve 207b, and the discarding valve 207c, and transfers the RO water produced by the RO water production device 7 to the RO water chamber 42 (step S107). If the RO water produced by the RO water production device 7 is transferred to the RO water chamber 42 in step S108 (YES in step S108), the CPU 48a proceeds the process to step S109 as is.

In step S109, the CPU 48a determines whether or not a predetermined amount (about 9 L) of reagent is accommodated in the reagent tank 47 based on the output signal of the float switch 106 (step S109). That is, whether or not the amount of reagent in the reagent tank 47 reached a predetermined amount is determined as a result of supplying the reagent to the reagent tank 47 in the second reagent supply process.

If a predetermined amount (about 9 L) of reagent is not accommodated in the reagent tank 47 in step S109, that is, if the amount of reagent in the reagent tank 47 still has not reached about 9 L even by the second reagent supply process (NO in step S109), the CPU 48a returns the process to step S104, and again executes the second reagent supply process. The produced RO water and the high concentration reagent are mixed to prepare the reagent while producing the RO water, and the prepared reagent is supplied to the reagent tank 47 until the amount of reagent in the reagent tank 47 reaches about 9 L.

If a predetermined amount (about 9 L) of reagent is accommodated in the reagent tank 47 in step S109, that is, if the amount of reagent in the reagent tank 47 reached about 9 L (i.e., maximum amount of reagent that can be accommodated in the reagent tank 47) (YES in step S109), the CPU 48a proceeds the process to step S110.

In step S110, the CPU 48a determines whether or not a predetermined amount (about 800 mL) of RO water is accommodated in the RO water chamber 42 based on the output signal of the float switch 101 (step S110).

If a predetermined amount of RO water is not accommodated in the RO water chamber 42 in step S110 (NO in step S110), the CPU 48a determines whether or not the RO water produced by the RO water production device 7 is transferred to the RO water chamber 42 (step S111). That is, whether or not the RO water produced by the RO water production device 7 is discarded is determined, as will be hereinafter described. Specifically, the RO water produced by the RO water production device 7 is transferred to the RO water chamber 42 if the flow-in control valve 207a is opened, the supply valve 207b is opened, and the discarding valve 207c is closed. Therefore, in step S111, whether or not a state in which the flow-in control valve 207a is opened, the supply valve 207b is opened, and the discarding valve 207c is closed is determined. If the RO water produced by the RO water production device 7 is not transferred to the RO water chamber 42, that is, if the RO water produced by the RO water production device 7 is discarded in step S111 (NO in step S111), the CPU 48a controls each valve to open the flow-in control valve 207a, open the supply valve 207b, and close the discarding valve 207c to start the transfer of the RO water produced by the RO water production device 7 to the RO water chamber 42 (step S112), and returns the process to step S110 to again determine whether or not a predetermined amount (about 800 mL) of RO water is accommodated in the RO water chamber 42 (step S110).

If the RO water produced by the RO water production device 7 is transferred to the RO water chamber 42, that is, if the RO water produced by the RO water production device 7 is not discarded in step S111 (YES in step S111), the CPU 48a returns the process to step S110 and repeats the processes of steps S110 and S111 until the RO water in the RO water chamber 42 reaches a predetermined amount.

If a predetermined amount (about 800 mL) of RO water is accommodated in the RO water chamber 42 in step S110 (YES in step S110), the CPU 48a determines whether or not a first predetermined time (30 minutes) has elapsed from the start of the RO water production (step s113). The RO water production is started with the transmission of the command to start the production of the RO water to the RO water production device 7. If the first predetermined time (30 minutes) has elapsed from the transmission of the command to start the production of the RO water in step S113 (YES in step S113), the CPU 48a transmits a command to the RO water production device 7 to stop the RO water production by the RO water production device 7 (step S114) and terminates the process. The RO water production device 7 then shifts to the standby state.

If the first predetermined time (30 minutes) has not yet elapsed from the start of the RO water production in step S106 (NO in step S113), the CPU 48a determines whether or not the RO water produced by the RO water production device 7 is transferred to the RO water chamber 42 (step S115). That is, whether or not the RO water produced by the RO water production device 7 is discarded is determined, as will be hereinafter described. Similar to step S111, in this process, whether or not a state in which the flow-in control valve 207a is opened, the supply valve 207b is opened, and the discarding valve 207c is closed is determined. If the RO water produced by the RO water production device 7 is not transferred to the RO water chamber 42, that is, if the RO water produced by the RO water production device 7 is discarded in step S115 (NO in step S115), the CPU 48a returns the process to step S109 and determines whether or not a predetermined amount (about 9 L) of reagent is accommodated in the reagent tank 47 (step S109). In a state a predetermined amount of RO water is stored in the RO water chamber 42, the reagent may be consumed by the blood analyzer 1 and the amount of reagent in the reagent tank 47 may become less than a predetermined amount (about 9 L). In the process of step S109, whether or not the reagent is consumed is determined. If the amount of reagent in the reagent tank 47 is reduced (NO in step S109), the CPU 48a proceeds the process to step S104 and executes the second reagent supply process. A new reagent is thereby prepared by the reagent preparation apparatus 4, and such reagent is supplied to the reagent tank 47.

If the RO water produced by the RO water production device 7 is transferred to the RO water chamber 42 in step S115 (YES in step S115), the CPU 48a controls the flow-in control valve 207a, the supply valve 207b, and the discarding valve 207c to stop the transfer of the RO water produced by the RO water production device 7 to the RO water chamber 42, and discards the RO water introduced from the RO water production device 7 to the reagent preparation apparatus 4 from the discarding port 503 (step S116). In the RO water production device 7, the preparation operation is carried out for every start if start and stop of the production of the RO water are repeated in a short time of within a first predetermined time, and time is required for the preparation operation, and hence it is not preferable. In the reagent preparation apparatus 4 according to the present embodiment, the RO water production is not stopped in a short time of within a first predetermined time from the start of the RO water production according to the operation described above, and hence it is preferable. The water leakage that occurs when the RO water is introduced into the RO water chamber 42 beyond the capacity of the RO water chamber 42 is prevented by discarding the RO water introduced from the RO water production device 7.

When the supply of RO water to the RO water chamber 42 is stopped in step S116, the CPU 48a returns the process to step S109, and determines whether or not a predetermined amount (about 9 L) of reagent is accommodated in the reagent tank 47 (step S109). Therefore, the RO water is continuously produced until the first predetermined time (30 minutes) has elapsed from the start of the RO water production when a predetermined amount (about 9 L) of reagent is accommodated in the reagent tank 47 and a predetermined amount (about 800 mL) of RO water is accommodated in the RO water chamber 42, and the produced RO water is discarded. When the first predetermined time (30 minutes) has elapsed from the start of the RO water production, the production of RO water is stopped and wasteful RO water production is suppressed.

The RO water is not supplied to the RO water chamber 42 in a state a predetermined amount (about 800 mL) of RO water is stored in the RO water chamber 42. The quality of the RO water in the RO water chamber 42 may degrade if a second predetermined time (eight hours) or longer has elapsed. In the reagent preparation apparatus 4 according to the present embodiment, the RO water in which the second predetermined time (eight hours) has elapsed from when stored in the RO water chamber 42 is discarded in the following manner. The RO water with degraded water quality thus can be prevented from being supplied.

If a predetermined amount (about 9 L) of reagent is accommodated in the reagent tank 47 in step S101 (YES in step S101), that is, if the reagent is not supplied from the reagent tank 47 to the blood analyzer 1, the CPU 48a determines whether or not the second predetermined time (eight hours) has elapsed from when the supply of RO water to the RO water chamber is stopped (step S117). If the second predetermined time (eight hours) has not elapsed from when the supply of the RO water to the RO water chamber is stopped in step S117 (NO in step S117), the CPU 48a terminates the process.

If the second predetermined time (eight hours) has elapsed from when the supply of the RO water to the RO water chamber is stopped in step S117 (YES in step S117), the CPU 48a opens the electromagnetic valves 204 and 205 to discard the RO water in the RO water chamber 42 (step S118).

After all the RO water in the RO water chamber 42 is discarded, the CPU 48a controls the RO water production device 7 to start the production of the RO water (step S119), and controls the flow-in control valve 207a, the supply valve 207b, and the discarding valve 207c to transfer the RO water produced by the RO water production device 7 to the RO water chamber 42 (step S120). After the supply of the RO water to the RO water chamber 42 is started, the CPU 48a proceeds to step S110, and the CPU 48a determines whether or not a predetermined amount (about 800 mL) of RO water is accommodated in the RO water chamber 42 based on the output signal of the float switch 101 (step S110).

According to the configuration described above, the reagent preparation apparatus 4 according to the present embodiment causes the RO water production device 7 to continue to produce RO water until elapse of a first predetermined time (30 minutes) from when the RO water production device 7 starts the RO water production even after the RO water is supplied from the RO water production device 7 to the RO water chamber 42, and a predetermined amount (about 800 mL) of RO water is stored in the RO water chamber 42. In the RO water production device 7 according to the present embodiment, the production speed of the RO water is about 5 L/hour, and it takes about ten minutes until a predetermined amount (about 800 mL) of RO water is stored in the empty RO water chamber. The RO water production device 7 requires preparation operation such as the cleaning of the RO film for starting the RO water production and the cleaning of the flow path of the RO water until supplying to the reagent preparation apparatus 4, where if start and stop of the RO water production are repeated frequently, the period of the preparation operation (about 5 minutes in the RO water production device 7 according to the present embodiment) is required each time and the RO water production cannot be efficiently carried out. In the reagent preparation apparatus 4 according to the present embodiment, the RO water production device 7 continues to produce the RO water until elapse of the first predetermined time (30 minutes) from when the RO water production device 7 starts the RO water production, and hence the RO water can be immediately supplied when there is a need to supply the RO water to the RO water chamber 42 within the first predetermined time, and the frequency of start and stop of the RO water production by the RO water production device 7 can be suppressed. The process of reagent preparation thus can be efficiently carried out. The blood analyzer 1 performs the measurement continuously and consumes reagent during the period of the preparation operation for starting the RO water production, where the reagent to be supplied to the blood analyzer 1 can be suppressed from lacking. In the present embodiment, the first predetermined time is 30 minutes or a time sufficiently longer than about 15 minutes, which is at least the time until a predetermined amount (about 800 mL) of RO water is accommodated in the RO water chamber 42 from the start of supply of the RO water to the RO water chamber 42. The first predetermined time is obtained experimentally so that the device lifespan of the RO water production device 7 becomes long according to the specification of the reagent preparation apparatus 4.

In the present embodiment, the RO water production device 7 produces the RO water if a predetermined amount (about 800 mL) of RO water is not accommodated in the RO water chamber 42. In the present embodiment, about 288 mL of RO water is used for one reagent preparation, and thus the reagent preparation can be carried out two times if about 800 mL of RO water is accommodated in the RO water chamber 42. Therefore, at least one reagent preparation can be immediately carried out when the RO water in the RO water chamber 42 is reduced and a predetermined amount (about 800 mL) is not satisfied from a state in which about 800 mL of RO water is accommodated in the RO water chamber 42 and instruction is made from the reagent preparation apparatus 4 to the RO water production device 7 to start the production of the RO water. In other words, at least one reagent preparation can be immediately carried out and the reagent preparation can be efficiently executed even if there is a preparation period for the production of the RO water.

In the present embodiment, if a predetermined amount (about 800 mL) of RO water is accommodated in the RO water chamber, and a first predetermined time (30 minutes) has elapsed from the start of the production of the RO water (YES in step S111), the RO water production by the RO water production device 7 is stopped. Thus, the RO water production device 7 can be prevented from continuously producing the RO water unnecessarily for a long time while efficiently carrying out the RO water production.

In the present embodiment, if a predetermined amount (about 800 mL) of RO water is accommodated in the RO water chamber 42, the flow-in control valve 207a, the supply valve 207b, and the discarding valve 207c are controlled, and the RO water produced by the RO water production device 7 is discarded. That is, since the RO water is discarded in the flow path before the RO water chamber 42, the water leakage can be prevented with a simple control without making the amount capable of accommodating the RO water in the RO water chamber greater than a predetermined amount for causing the RO water production device 7 to start producing the RO water compared to when the RO water is discarded in the flow path after the RO water chamber 42.

OTHER EMBODIMENTS

In the embodiments described above, the configuration in which the blood analyzer 1 receives the supply of reagents from the reagent preparation apparatus 4 and analyzes the blood sample using the relevant reagent has been described, but this is not the sole case. The reagent preparation apparatus 4 may prepare the reagent for urine sediment analysis from the RO water and the high concentration reagent, and supply the reagent to other sample analyzers such as supply the prepared reagent to the urine sediment analyzer for analyzing the urine sample using the relevant reagent.

In the embodiments described above, the configuration in which only one blood analyzer 1 is connected to the reagent preparation apparatus 4 has been described, but this is not the sole case. A plurality of blood analyzers 1 may be connected to the reagent preparation apparatus 4.

In the embodiments described above, the configuration in which the RO water chamber 42 is arranged inside the reagent preparation apparatus 4 has been described, but this is not the sole case. The RO water chamber 42 may be arranged in the RO water production device 7, and the RO water may be supplied therefrom to the first diluting chamber 43 or the second diluting chamber 44. The RO water chamber 42 may be arranged exterior to the reagent preparation apparatus 4 and the RO water production device 7 as an RO water tank.

In the embodiments described above, the configuration in which the supply destination of the RO water produced by the RO water production device 7 is switched to either the RO water chamber 42 or the discarding flow path 502 by the three electromagnetic valves 207a, 207b, 207c has been described, but this is not the sole case. The configuration in which the electromagnetic valve 207a is not arranged, and the supply destination of the RO water produced by the RO water production device 7 is switched to either the RO water chamber 42 or the discarding flow path 502 by the two electromagnetic valves 207b, 207c may be adopted, or the configuration in which the supply destination of the RO water is switched to either the RO water chamber 42 or the discarding flow path 502 by one electromagnetic valve, which is a three-way valve, may be adopted.

In the embodiments described above, the configuration in which the flow path 502 for discarding the RO water is arranged, and the RO water is discarded without being supplied to the RO water chamber 42 has been described, but this is not the sole case. The configuration in which the flow path 502 is not arranged, and the RO water accommodated in the RO water chamber is discarded using the discarding flow path connected to the RO water chamber while supplying the RO water to the RO water chamber 42 may be adopted.

In the embodiments described above, the configuration in which the supply destination of the RO water accommodated in the RO water chamber 42 is switched to one of the first diluting chamber 43, the second diluting chamber 44, or the discarding flow path by the two electromagnetic valves 205, 208 has been described, but this is not the sole case. The configuration in which the discarding flow path is branched from the middle of the flow path 302 for supplying the RO water from the RO water chamber 42 to the first diluting chamber 43 or the second diluting chamber 44, arranging one electromagnetic valve which is a three-way valve at the branch point, and switching the supply destination of the RO water to one of the first diluting chamber 43, the second diluting chamber 44, or the discarding flow path by the electromagnetic valve may be adopted.

In the embodiments described above, the reagent preparation apparatus 4 installed separate from the measurement section 2 has been described, but is not limited thereto. The reagent preparation apparatus may be arranged in the measurement section of the sample analyzer.

In the embodiments described above, the configuration in which the RO water production device 7 is arranged exterior to the reagent preparation apparatus 4 has been described, but this is not the sole case. The RO water production device may be arranged inside the reagent preparation apparatus as part of the reagent preparation apparatus.

In the embodiments described above, the configuration in which two diluting chambers (first diluting chamber 43 and second diluting chamber 44) are arranged has been described, but this is not the sole case. Only one mixing container (diluting chamber) may be arranged or three or more mixing containers (diluting chambers) may be arranged.

In the embodiments described above, the RO water amount (about 800 mL) of the RO water chamber 42 that becomes the reference for starting the supply of the RO water to the RO water chamber 42 and the water amount (about 800 mL) of the RO water chamber 42 that becomes the reference for stopping the supply of the RO water to the RO water chamber 42 are the same, but this is not the sole case. The RO water amount of both references may be differed. For instance, the water amount of the RO water chamber 42 that becomes the reference for starting the supply of the RO water to the RO water chamber 42 may be less than the RO water amount of the RO water chamber 42 that becomes the reference for stopping the supply of the RO water to the RO water chamber 42.

The reagent preparation apparatus 4 according to the embodiments causes the RO water production device 7 to continue to produce the RO water until elapse of a first predetermined time (30 minutes) from when the RO water production device 7 starts the RO water production even after the RO water is supplied from the RO water production device 7 to the RO water chamber 42 and the predetermined amount (about 800 mL) of RO water is stored in the RO water chamber 42. However, the present invention is not limited thereto. The first predetermined time may be experimentally obtained so that the device lifespan of the RO water production device 7 becomes long according to the specification of the reagent preparation apparatus 4. For instance, the first predetermined time may be from 20 minutes to 50 minutes, and more preferably from 25 minutes to 35 minutes.

What is claimed is:

1. A reagent preparation apparatus for supplying a reagent, prepared by mixing a concentrated reagent and purified water produced from water by a purified water production device including a valve configured to stop/start a supply of water into the purified water production device, to a sample measurement device for measuring a sample using the prepared reagent, the reagent preparation apparatus comprising:
    a reagent preparation unit comprising a purified water storage unit and a chamber,
        wherein the purified water storage unit is configured to store a predetermined amount of the purified water supplied from the purified water production device, and
        wherein the chamber is configured to mix the concentrated reagent and the purified water supplied from the purified water storage unit for preparing the reagent; and
    a processor, communicably connected to the purified water production device, and programmed to:
        transmit a start instruction for starting production of purified water to the purified water production device; and
        transmit a stop instruction for stopping the production of purified water to the purified water production device,
    wherein the processor is further programmed to control the purified water production device to continue producing the purified water until a predetermined time has elapsed from when the purified water production device starts the production of the purified water, by not transmitting the stop instruction to the purified water production device until the predetermined time has elapsed from the transmission of the start instruction, even if amount of purified water in the purified water storage unit reaches the predetermined amount, and
    wherein the purified water production device starts the production of purified water in response to a start instruction transmitted from the reagent preparation apparatus by opening the valve and stops the production of purified water in response to a stop instruction transmitted from the reagent preparation apparatus by closing the valve.

2. The reagent preparation apparatus according to claim 1, wherein
    the processor is further programmed to transmit the start instruction to the purified water production device when the amount of the purified water in the purified water storage unit does not reach the predetermined amount.

3. The reagent preparation apparatus according to claim 2, wherein
    the predetermined amount is greater than amount of purified water necessary for the reagent preparation unit to carry out one reagent preparation.

4. The reagent preparation apparatus according to claim 3, wherein
    the processor is further programmed to transmit the stop instruction to the purified water production device if the amount of purified water in the purified water storage unit is greater than or equal to the predetermined amount and the predetermined time has elapsed from the start of production of the purified water.

5. The reagent preparation apparatus according to claim 1, further comprising:
    a first flow path configured to supply the purified water from the purified water production device to the purified water storage unit; and
    a first valve configured to open/close the first flow path,
    wherein the processor is further programmed to control the first valve to close the first flow path so as to stop supplying of the purified water if the amount of the purified water in the purified water storage unit is greater than or equal to a predetermined amount.

6. The reagent preparation apparatus according to claim 1, further comprising
    a first discarding flow path configured to discard the purified water produced by the purified water production device,
    wherein the processor is further programmed not to transmit the stop instruction to the purified water production device while discarding the purified water by the first discarding flow path if the amount of the purified water in the purified water storage unit is greater than or equal to a predetermined amount.

7. The reagent preparation apparatus according to claim 6, further comprising
    a first flow path configured to supply the purified water from the purified water production device to the purified water storage unit, wherein
    the first discarding flow path is connected to the first flow path to discard the purified water introduced from the first flow path.

8. The reagent preparation apparatus according to claim 1, further comprising:
    a second flow path configured to supply the purified water from the purified water storage unit to the chamber;
    wherein the processor is further programmed to transmit the start instruction to the purified water production device if amount of purified water in the purified water storage unit has not reached the predetermined amount, and controls the second flow path so that the purified water stored in the purified water storage unit is not supplied to the chamber if the production of the purified water by the purified water production device is stopped and the reagent in the chamber is greater than or equal to a predetermined amount.

9. The reagent preparation apparatus according to claim 8, further comprising
    a second discarding flow path configured to discard the purified water stored in the purified water storage unit,
    wherein the processor is further programmed to cause the purified water storage unit to discharge the purified water stored in the purified water storage unit by the second discarding flow path if the production of the purified water by the purified water production device is stopped and the preparation of the reagent by the chamber has not been carried out for a second predetermined time longer than the predetermined time.

10. The reagent preparation apparatus according to claim 9, wherein the second flow path includes a second valve configured to switch a supply destination of the purified water stored in the purified water storage unit to either the chamber or the second discarding flow path.

11. The reagent preparation apparatus according to claim 1, further comprising:
   a reagent tank configured to store the reagent prepared by the chamber; and
   a third flow path configured to supply the reagent from the chamber to the reagent tank,
   wherein the processor is further programmed to control the third flow path to supply the reagent from the chamber to the reagent tank if amount of reagent in the reagent tank does not reach a predetermined amount.

12. The reagent preparation apparatus according to claim 11, wherein
   the processor is further programmed to transmit the start instruction to the purified water production device if amount of purified water in the purified water storage unit has not reached the predetermined amount, and
   to control the second flow path so that the purified water stored in the purified water storage unit is supplied to the chamber if the production of the purified water by the purified water production device is continued, the amount of reagent stored in the chamber is lower than a first reference value and the amount of reagent stored in the reagent tank is lower than a second reference value.

13. A reagent preparation system for supplying a reagent, prepared by a reagent preparation apparatus, to a sample measurement device for measuring a sample using the prepared reagent, the reagent preparation system comprising:
   a purified water production device configured to produce the purified water from water, wherein
      the purified water production device includes a valve configured to stop/start a supply of water into the purified water production device and
      the purified water production device starts the production of purified water in response to a start instruction transmitted from the reagent preparation apparatus by opening the valve and stops the production of purified water in response to a stop instruction transmitted from the reagent preparation apparatus by closing the valve; and
   a reagent preparation apparatus comprising:
      a reagent preparation unit comprising a purified water storage unit and a chamber,
         wherein the purified water storage unit is configured to store a predetermined amount of the purified water supplied from the purified water production device, and
         wherein the chamber is configured to mix the concentrated reagent and the purified water supplied from the purified water storage unit for preparing the reagent; and
      a processor, communicably connected to the purified water production device, and programmed to:
         transmit a start instruction for starting production of purified water to the purified water production device; and
         transmit a stop instruction for stopping the production of purified water to the purified water production device,
      wherein the processor is further programmed to control the purified water production device to continue producing the purified water until a predetermined time has elapsed from when the purified water production device starts the production of the purified water, by not transmitting the stop instruction to the purified water production device until the predetermined time has elapsed from the transmission of the start instruction, even if amount of purified water in the purified water storage unit reaches the predetermined amount.

14. The reagent preparation system according to claim 13, wherein the processor is further programmed to transmit the start instruction to the purified water production device when the amount of the purified water in the purified water storage unit does not reach the predetermined amount.

15. The reagent preparation system according to claim 14, wherein the predetermined amount is greater than amount of purified water necessary for the reagent preparation unit to carry out one reagent preparation.

16. The reagent preparation apparatus according to claim 3, wherein the predetermined amount is greater than amount of purified water necessary for the reagent preparation unit to carry out two reagent preparation and is less than amount of purified water necessary for the reagent preparation unit to carry out three reagent preparation.

17. The reagent preparation apparatus according to claim 16, further comprising a second chamber having similar configurations to the chamber.

18. The reagent preparation system according to claim 15, wherein the predetermined amount is greater than amount of purified water necessary for the reagent preparation unit to carry out two reagent preparation and is less than amount of purified water necessary for the reagent preparation unit to carry out three reagent preparation.

19. The reagent preparation system according to claim 18, wherein the purified water production device requires a third predetermined time for a preparing operation to start the production of the purified water.

* * * * *